United States Patent
Allen et al.

(10) Patent No.: US 9,694,206 B2
(45) Date of Patent: *Jul. 4, 2017

(54) RADIOTHERAPY AND IMAGING APPARATUS

(71) Applicant: Elekta AB (publ), Stockholm (SE)

(72) Inventors: John Allen, Haywards Heath (GB); Kevin Brown, Horsham (GB)

(73) Assignee: ELEKTA AB (PUBL), Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/285,301

(22) Filed: Oct. 4, 2016

(65) Prior Publication Data

US 2017/0021196 A1    Jan. 26, 2017

Related U.S. Application Data

(63) Continuation of application No. 13/035,364, filed on Feb. 25, 2011, now Pat. No. 9,480,858, which is a
(Continued)

(51) Int. Cl.
| | | |
|---|---|---|
| *A61B 5/05* | (2006.01) | |
| *A61N 5/10* | (2006.01) | |
| *G01R 33/48* | (2006.01) | |

(52) U.S. Cl.
CPC ......... *A61N 5/1049* (2013.01); *A61N 5/1042* (2013.01); *A61N 5/1045* (2013.01);
(Continued)

(58) Field of Classification Search
USPC .... 600/407, 410, 411, 413, 425, 427; 378/4, 378/15, 20, 196, 197
See application file for complete search history.

(56) References Cited

U.S. PATENT DOCUMENTS

| | | |
|---|---|---|
| 5,317,616 A | 5/1994 | Swerdloff et al. |
| 6,198,957 B1 | 3/2001 | Green |

(Continued)

FOREIGN PATENT DOCUMENTS

| | | |
|---|---|---|
| WO | 0007667 A1 | 2/2000 |
| WO | 03008986 A2 | 1/2003 |

(Continued)

OTHER PUBLICATIONS

Raaymakers et al., Integrating a 1.5 T MRI Scanner with a 6 MV Accelerator: Proof of Concept, Physics in Medicine and Biology, vol. 54, 2009, N229-N237.

(Continued)

*Primary Examiner* — Tse Chen
*Assistant Examiner* — Jason Ip
(74) *Attorney, Agent, or Firm* — Westman, Champlin & Koehler, P.A.; Z. Peter Sawicki; Amanda M. Prose (57) ABSTRACT

A radiotherapy system comprises a patient support, moveable along a translation axis, an imaging apparatus, comprising a first magnetic coil and a second magnetic coil, the first and second magnetic coils having a common central axis parallel to the translation axis, and being displaced from one another along the central axis to form a gap therebetween, the imaging apparatus being configured to obtain an image of a patient on the patient support, a source of radiation mounted on a chassis, the chassis being rotatable about the central axis and the source being adapted to emit a beam of radiation through the gap along a beam axis that intersects with the central axis, a multi-leaf collimator comprising a plurality of elongate leaves movable between at least a withdrawn position in which the leaf lies outside the beam, and an extended position in which the leaf projects across the beam, and a radiation detector mounted to the chassis opposite the source, the radiation detector having a plurality of detector elements aligned with the elongate leaves when projected onto an isocentric plane.

9 Claims, 5 Drawing Sheets

Related U.S. Application Data continuation-in-part of application No. 12/704,986, filed on Feb. 12, 2010, now abandoned.

(52) U.S. Cl.
CPC ......... *A61N 5/1048* (2013.01); *A61N 5/1071* (2013.01); *A61N 5/1081* (2013.01); *G01R 33/4808* (2013.01); *A61N 2005/1054* (2013.01); *A61N 2005/1055* (2013.01)

(56) References Cited

U.S. PATENT DOCUMENTS

| | | |
|---|---|---|
| 6,366,798 B2 | 4/2002 | Green |
| 6,438,202 B1 | 8/2002 | Olivera et al. |
| 6,725,078 B2 | 4/2004 | Bucholz et al. |
| 7,399,119 B2 | 7/2008 | Chao et al. |
| 2005/0197564 A1 | 9/2005 | Dempsey |
| 2005/0267350 A1 | 12/2005 | McKinnon |
| 2006/0067480 A1 | 3/2006 | Juschka et al. |
| 2006/0182326 A1 | 8/2006 | Schildkraut et al. |
| 2008/0208036 A1 | 8/2008 | Amies et al. |
| 2009/0124887 A1 | 5/2009 | Roell et al. |

FOREIGN PATENT DOCUMENTS

| | | |
|---|---|---|
| WO | 2005081842 A2 | 9/2005 |
| WO | 2009155700 A1 | 12/2009 |

OTHER PUBLICATIONS

European Search Report, Apr. 20, 2011.
European Examination Report; 11000966.9 (Mar. 28, 2012).

PRIOR ART

RADIOTHERAPY AND IMAGING APPARATUS

CROSS-REFERENCE TO RELATED APPLICATION

The present application is a continuation of and claims priority of U.S. patent application Ser. No. 13/035,364, filed Feb. 25, 2011, which is a continuation-in-part of and claims priority of U.S. patent application Ser. No. 12/704,986, filed Feb. 12, 2010, the contents of which are hereby incorporated by reference in their entirety.

FIELD OF THE INVENTION

The present invention relates to radiotherapy apparatus, and particularly to a radiotherapy apparatus comprising a magnetic resonance imaging (MRI) apparatus.

BACKGROUND ART

It is known that exposure of human or animal tissue to ionising radiation will kill the cells thus exposed. This finds application in the treatment of pathological cells, for example. In order to treat tumours deep within the body of the patient, the radiation must however penetrate the healthy tissue in order to irradiate and destroy the pathological cells. In conventional radiation therapy, large volumes of healthy tissue can thus be exposed to harmful doses of radiation, resulting in prolonged recovery periods for the patient. It is, therefore, desirable to design a device for treating a patient with ionising radiation and treatment protocols so as to expose the pathological tissue to a dose of radiation which will result in the death of those cells, whilst keeping the exposure of healthy tissue to a minimum.

Several methods have previously been employed to achieve the desired pathological cell-destroying exposure whilst keeping the exposure of healthy cells to a minimum. Many methods work by directing radiation at a tumour from a number of directions, either simultaneously from multiple sources or multiple exposures from a single source. The intensity of radiation emanating from each direction is therefore less than would be required to actually destroy cells (although still sufficient to damage the cells), but where the radiation beams from the multiple directions converge, the intensity of radiation is sufficient to deliver a therapeutic dose. By providing radiation from multiple directions, the amount of radiation delivered to surrounding healthy cells can be minimized.

The shape of the beam varies. For single-source devices, cone beams centred on the isocentre are common, while fan beams are also employed (for example as shown in U.S. Pat. No. 5,317,616).

Of course it is also important that the radiation should be accurately targeted on the region that requires treatment. For this reason, patients are required to remain still for the duration of the therapy session, to minimize the risk of damage to healthy tissue surrounding the target region. However, some movement is inevitable, e.g. through breathing, or other involuntary movements.

To overcome this problem, it is known to integrate an image acquisition system with the radiotherapy apparatus, to provide real-time imaging of the region and ensure that the radiation emitted by the radiotherapy apparatus tracks any movement of the patient. However, the choice of imaging system is in general limited by the radiotherapy apparatus in which it is installed, and in particular by the geometry. For example, magnetic resonance imaging (MRI) systems require magnetic coils to be placed around the patient. However, these coils will act to block therapeutic radiation from reaching the patient.

What is required is an integrated radiotherapy system that delivers high-quality in both the imaging and treatment of a patient.

SUMMARY OF THE INVENTION

Currently a number of different devices are used for quality assurance (QA) and in-vivo dosimetry with radiotherapy machines.

Electronic portal imaging device (EPID)—this is used to detect the exit dose from the patient and calculate the dose deposited in the patient using back projection methods.

CT detector on Tomotherapy—the binary multi-leaf collimator used on Tomotherapy is shaped as a narrow slit. The radiation fluence from the slit can be measured using a one-dimensional CT detector which is positioned on the exit side of patient. The dose deposited in the patient can be calculated using back projection methods.

Diodes—these are used to measure the entrance or exit dose by attaching them directly on the patient's surface.

However, none of these systems is ideally suited to use with a radiotherapy system comprising an MRI imaging apparatus. The MRI system has a narrow window through which the radiation can pass to reach the target. The MRI system has a narrow bore so it is not possible to adjust the position of the patient so that the target is in the centre of the field. Furthermore an offset target will require different parts of the width of the collimator to be used as the gantry rotates.

The inventors of the present invention have overcome the problems associated with conventional integrated radiotherapy and imaging systems, by providing a radiotherapy MRI system with a multi-leaf collimator (MLC) and a radiation detector having a plurality of detector elements aligned to the width of the leaves of the MLC when projected onto the isocentric plane. The radiation detector is not a portal imager, as the MRI system is the imaging system. Rather, the radiation detector provides QA and in-vivo dosimetry, and therefore need not have a high resolution.

The present invention therefore provides, according to one aspect, a radiotherapy system comprising a patient support, moveable along a translation axis, an imaging apparatus, comprising a first magnetic coil and a second magnetic coil, the first and second magnetic coils having a common central axis parallel to the translation axis, and being displaced from one another along the central axis to form a gap therebetween, the imaging apparatus being configured to obtain an image of a patient on the patient support, a source of radiation mounted on a chassis, the chassis being rotatable about the central axis and the source being adapted to emit a beam of radiation through the gap along a beam axis that intersects with the central axis, a multi-leaf collimator comprising a plurality of elongate leaves movable between at least a withdrawn position in which the leaf lies outside the beam, and an extended position in which the leaf projects across the beam, and a radiation detector mounted to the chassis opposite the source, the radiation detector having a plurality of detector elements aligned with the elongate leaves when projected onto an isocentric plane.

In an embodiment, the radiation detector comprises a plurality of detector elements, columns of which may be aligned with a particular elongate leaf. The columns may be spaced between about 2 mm and about 10 mm apart when projected onto an isocentric plane. The radiation detector may be mounted outside the first and second magnetic coils.

In an embodiment, the system further comprises a multi-leaf collimator comprising a plurality of elongate leaves disposed with their longitudinal directions substantially aligned with the first direction and movable in that direction between a withdrawn position in which the leaf lies outside the beam, an extended position in which the leaf projects into the beam, and a plurality of intermediate positions therebetween.

The multi-leaf collimator disclosed above may comprise a respective plurality of actuators, for moving the plurality of elongate leaves.

In one embodiment, the chassis is continuously rotatable about the central axis. In this embodiment, the patient support may be configured to move along the translation axis as the chassis rotates about the central axis, resulting in a helical radiation delivery pattern. Such a pattern is known to produce high quality dose distributions.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
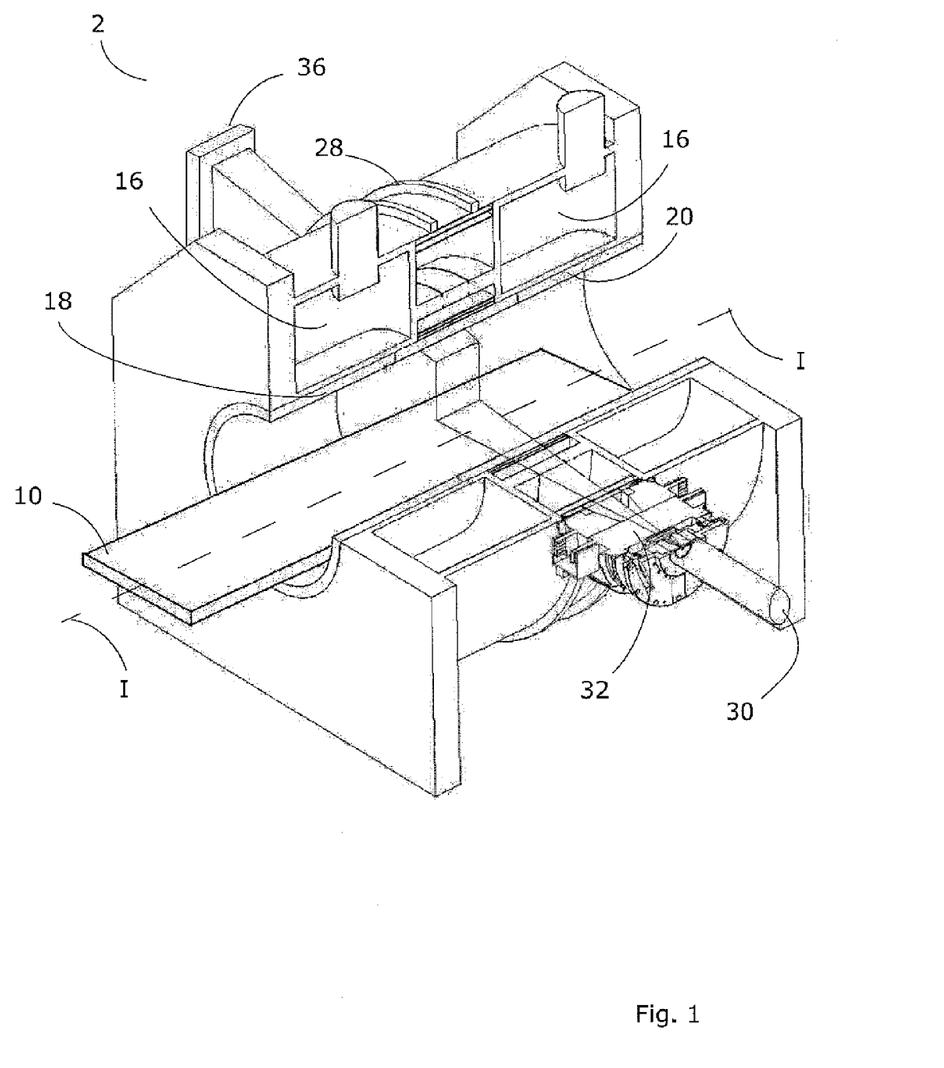
FIG. 1 shows a radiotherapy system according to embodiments of the present invention.

FIG. 1 shows a system according to embodiments of the present invention, comprising a radiotherapy apparatus and a magnetic resonance imaging (MRI) apparatus. The radiotherapy apparatus 6 and MRI apparatus 4 are shown schematically in FIG. 2.

The system includes a couch 10, for supporting a patient in the apparatus. The couch 10 is movable along a horizontal, translation axis (labelled "I"), such that a patient resting on the couch is moved into the radiotherapy and MRI apparatus. In one embodiment, the couch 10 is rotatable around a central vertical axis of rotation, transverse to the translation axis, although this is not illustrated. The couch 10 may form a cantilever section that projects away from a support structure (not illustrated). In one embodiment, the couch 10 is moved along the translation axis relative to the support structure in order to form the cantilever section, i.e. the cantilever section increases in length as the couch is moved and the lift remains stationary. In another embodiment, both the support structure and the couch 10 move along the translation axis, such that the cantilever section remains substantially constant in length, as described in our U.S. patent application Ser. No. 11/827,320 filed on 11 Jul. 2007.

Figure 2:
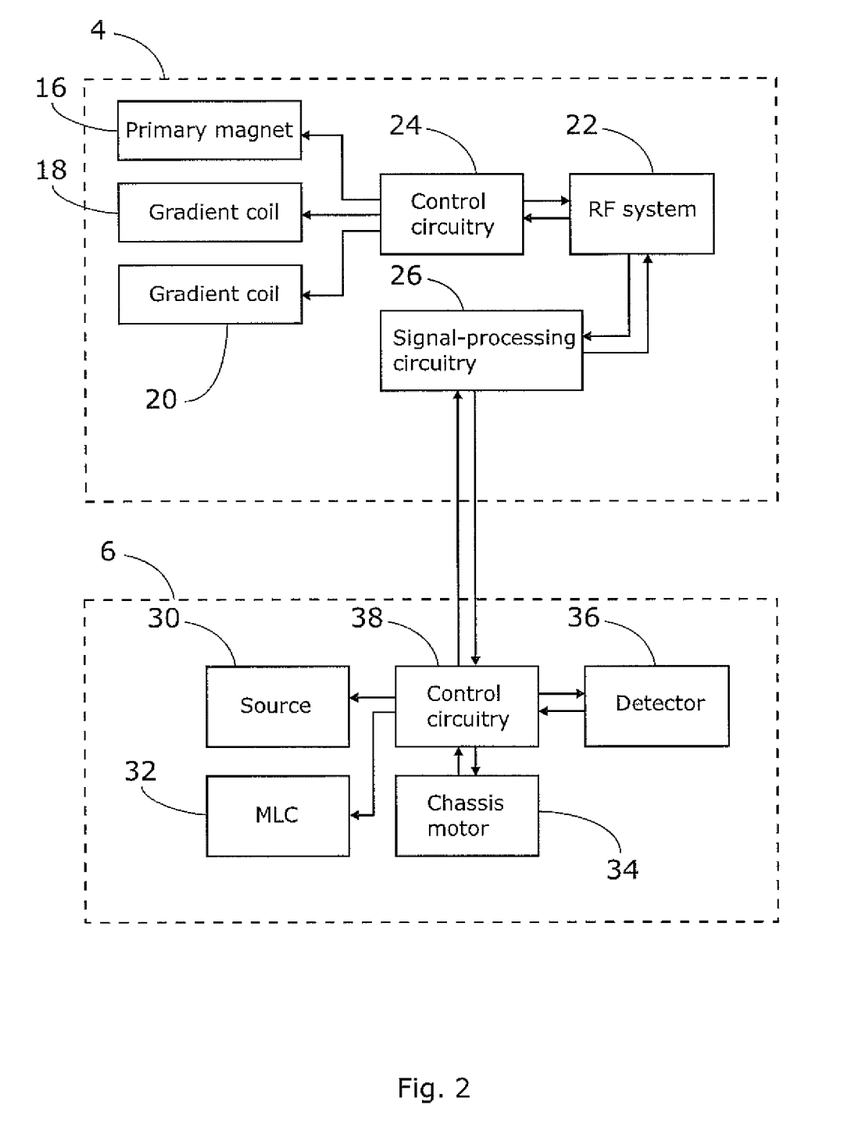
FIG. 2 is a schematic diagram of aspects of the radiotherapy system according to embodiments of the present invention.

As mentioned above, the system 2 also comprises an MRI apparatus 4, for producing real-time imaging of a patient positioned on the couch 10. The MRI apparatus includes a primary magnet 16 which acts to generate the so-called "primary" magnetic field for magnetic resonance imaging. That is, the magnetic field lines generated by operation of the magnet 16 run substantially parallel to the central translation axis I. The primary magnet 16 consists of one or more coils with an axis that runs parallel to the translation axis I. The one or more coils may be a single coil or a plurality of coaxial coils of different diameter, as illustrated. In one embodiment, the one or more coils in the primary magnet 16 are spaced such that a central window of the magnet 16 is free of coils. In other embodiments, the coils in the magnet 16 may simply be thin enough that they are substantially transparent to radiation of the wavelength generated by the radiotherapy apparatus. The magnet 16 may further comprise one or more active shielding coils, which generates a magnetic field outside the magnet 16 of approximately equal magnitude and opposite polarity to the external primary magnetic field. The more sensitive parts of the system 2, such as the accelerator, are positioned in this region outside the magnet 16 where the magnetic field is cancelled, at least to a first order. The MRI apparatus 4 further comprises two gradient coils 18, 20, which generate the so-called "gradient" magnetic field that is superposed on the primary magnetic field. These coils 18, 20 generate a gradient in the resultant magnetic field that allows spatial encoding of the protons so that their position can be determined from the frequency at which resonance occurs (the Larmor frequency). The gradient coils 18, 20 are positioned around a common central axis with the primary magnet 16, and are displaced from one another along that central axis. This displacement creates a gap, or window, between the two coils 18, 20. In an embodiment where the primary magnet 16 also comprises a central window between coils, the two windows are aligned with one another.

An RF system 22 transmits radio signals at varying frequencies towards the patient, and detects the absorption at those frequencies so that the presence and location of protons in the patient can be determined. The RF system 22 may include a single coil that both transmits the radio signals and receives the reflected signals, dedicated transmitting and receiving coils, or multi-element phased array coils, for example. Control circuitry 24 controls the operation of the various coils 16, 18, 20 and the RF system 22, and signal-processing circuitry 26 receives the output of the RF system, generating therefrom images of the patient supported by the couch 10.

As mentioned above, the system 2 further comprises a radiotherapy apparatus 6 which delivers doses of radiation to a patient supported by the couch 10. The majority of the radiotherapy apparatus 6, including at least a source of radiation 30 (e.g. an x-ray source) and a multi-leaf collimator (MLC) 32, is mounted on a chassis 28. The chassis 28 is continuously rotatable around the couch 10 when it is inserted into the treatment area, powered by one or more chassis motors 34. In the illustrated embodiment, a radiation detector 36 is also mounted on the chassis 28 opposite the radiation source 30 and with the rotational axis of the chassis positioned between them. The radiotherapy apparatus 6 further comprises control circuitry 38, which may be integrated within the system 2 shown in FIG. 1 or remote from it, and controls the source the radiation source 30, the MLC 32 and the chassis motor 34.

The radiation source 30 is positioned to emit radiation through the window defined by the two gradient coils 18, 20, and also through the window defined in the primary magnet 16. According to embodiments of the present invention, the source 30 emits so-called "fan beams" of radiation. The radiation beam is collimated with appropriate shielding prior to arrival at the MLC 32, by which time it is already "letterbox-shaped" in order to pass through the MLC housing as described in greater detail below. That is, the radiation beam is relatively narrow in one dimension parallel to the axis of rotation of the chassis 28 (such as 15 cm at a radius of 60 cm), and is relatively wide in a dimension that is transverse to the axis of rotation of the chassis. Thus, the beam takes the fan shape that gives it its name. It is this fan-shaped beam that is ideally suited to the geometry of the system 2, in which two gradient coils 18, 20 are displaced from one another in order to allow the radiation access to the patient. A fan-shaped beam provides substantial radiation to the patient through the narrow window, meaning that the gradient coils 18, 20 can be placed closer together than with conventional integrated radiotherapy/imaging systems. This allows the gradient coils 18, 20 to generate stronger gradient fields than would otherwise be the case, increasing the quality of the images obtained by the MRI apparatus 4. However, the present invention also contemplates beams of radiation taking different shapes such as cone beams, etc.

The radiation detector 36 is optimised for the geometry shown in FIG. 1, and can be used for QA and in-vivo dosimetry. The detector 36 is positioned outside the magnetic coils 16, 18, 20 on the chassis 28, aligned with the radiation beam exit. It therefore has a fixed position relative to the radiation source 30 and MLC 32.

Owing to the fact that it is outside the coils 16, 18, 20 the effect of scattered radiation will be dominated by the materials in the magnet 16, which are a constant and therefore comparatively easy to model. This is unlike existing electronic portal imaging device (EPID) schemes which are subject to varying scatter from the patient due to differing patient geometries which is difficult to predict.

Due to the large transverse size of the detector 36, it uses individual detector elements (not illustrated). These can either be diodes, ion chambers or similar. Because the detector 36 is used only for quality assurance (QA) and in-vivo dosimetry rather than patient imaging (the MRI apparatus 4 being the primary patient imager), the pitch of the detecting elements can be relatively coarse, i.e. substantially equal to the width of the leaves of the MLC 32 when projected onto the isocentric plane. The width of the leaves is defined by the design of the MLC and may be between 2 mm and 10 min when projected onto the isocentric plane).

The detector 36 further comprises elements to perform some of the machine QA on the MLC 32, i.e. detecting that the leaves of the MLC are correctly positioned. Columns of these detector elements will typically be at the pitch of the leaves of the MLC. There may be a number of columns of detector elements to allow the leaves to be detected at discrete positions. These columns of detector elements are ideally suited to an MLC which is fixed in its orientation, because the leaves will always be aligned to particular columns of detector elements.

In operation, a patient is placed on the couch 10 and the couch is inserted into the treatment area defined by the magnetic coils 16, 18 and the chassis 28. The control circuitry 38 controls the radiation source 30, the MLC 32 and the chassis motor to deliver radiation to the patient through the window between the coils 16, 18. The control circuitry 38 controls the source to deliver radiation in a fan beam, in the usual pulsed manner. The chassis motor 34 is controlled such that the chassis 28 rotates about the patient, meaning the radiation can be delivered from different directions. The MLC 32 is controlled to take different shapes, thereby altering the shape of the beam as it will reach the patient. Simultaneously with rotation of the chassis 28 about the patient, the couch 10 may be moved along a translation axis into or out of the treatment area (i.e. parallel to the axis of rotation of the chassis). With this simultaneous motion a helical radiation delivery pattern is achieved, known to produce high quality dose distributions.

The MRI apparatus 4, and specifically the signal-processing circuitry 26, delivers real-time (or in practice near real-time, after a delay in the order of milliseconds) images of the patient to the control circuitry 38. This information allows the control circuitry to adapt the operation of the source 30, MLC 32 and/or chassis motor 34, such that the radiation delivered to the patient accurately tracks the motion of the patient, for example due to breathing.

Figure 3:
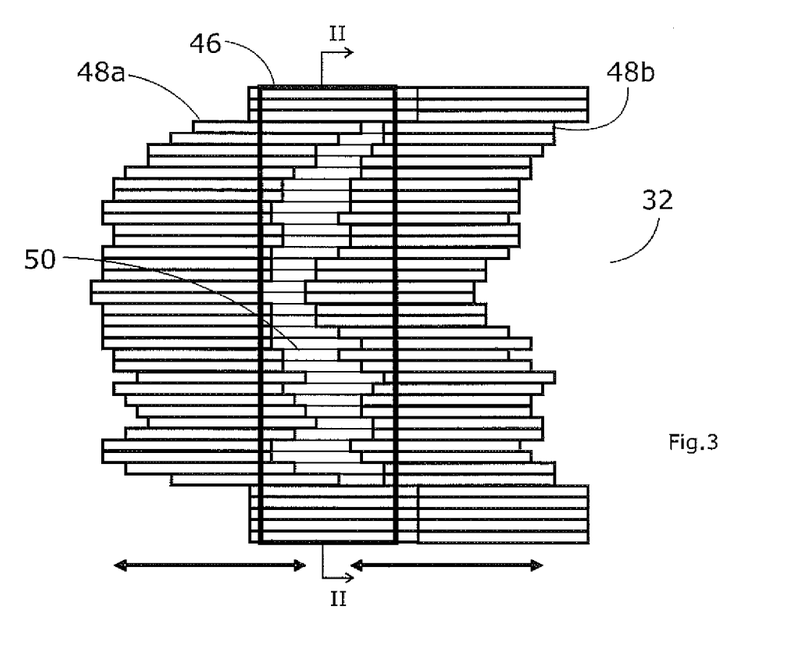
FIG. 3 shows a multi-leaf collimator according to another embodiment of the present invention.

FIG. 3 shows an MLC 32 according to an embodiment of the present invention. In this embodiment, the collimator 32 comprises a housing 46 which is effectively shaped as an elongate rectangular aperture. Pairs of leaves (for example as indicated with reference numerals 48*a*, 48*b*) are located along the housing 46, and are movable into and out of the aperture in a substantially continuous number of positions by action of a plurality of actuators. The actuators may be operated by electromagnetic motors, placed outside the coils 16, 18, 20 to minimize interference with the magnetic fields present in the MRI apparatus 4. At one extreme, each leaf may be positioned entirely outside the aperture; at the other, each leaf may be positioned entirely within the aperture. As illustrated, each leaf may be separately controllable to move into and out of the housing (i.e. the movement of the leaves in each pair is not linked). This embodiment allows the target region to be tracked more accurately, as it does not assume that the target is in the centre of the field of view.

The MLC 32 is fixed in its orientation and has a maximum field size defined by the shape of the housing 46 that is relatively small in the longitudinal direction (matched to the width of the gap between the two magnetic coils 18, 20, typically 15 cm at a radius of 60 cm) and relatively large in the transverse direction.

In one embodiment, the MLC 32 does not rotate. This makes the construction simpler and cheaper. It also makes the geometry more stable and easier to calibrate, and quality assurance easier to achieve. To overcome this lack of rotation, however, the leaves 48 are thinner than in conventional MLCs. To prevent these thin leaves from bending under their own weight they can be supported across the treatment field. The MLC 32 comprises a plurality of supports 50 that stretch across the housing, as shown most clearly in the cross-section view of FIG. 4. Each leaf 48 is shaped so that a relatively narrow portion slots between a pair of adjacent supports 50. Two shoulders are then defined between the relatively narrow region of each leaf and the relatively wide region, which sit on top of the supports 50. The provision of supports 50 is possible because there is no possibility of a field defining light in the MRI linac or the use of electrons, as the magnet 16 prevents it. The additional material introduced by use of the supports 50 can be insignificant compared to the material already in the magnet, and so does not further interfere with the therapeutic radiation delivered to the patient. For example, the leaves are typically manufactured from a material with a relatively high atomic number (e.g. tungsten) and represent a considerable barrier to the radiation due to their relatively thick cross section along the beam axis. In contrast, the supports 50 are relatively thin in that direction, and may be made from a material with a relatively low atomic number (e.g. aluminium). The combination of both these factors means that the supports 50 present a negligible barrier to the radiation, even though they are fixed across the beam's path. In alternative embodiments, a sheet of material (e.g. aluminium) may be placed over the exit to the MLC 32, in order to support the leaves. The sheet is again thin enough that it does not present a significant barrier to the radiation. The supports 50 may be grooves in the sheet, or raised projections extending from the sheet.

Figure 4:
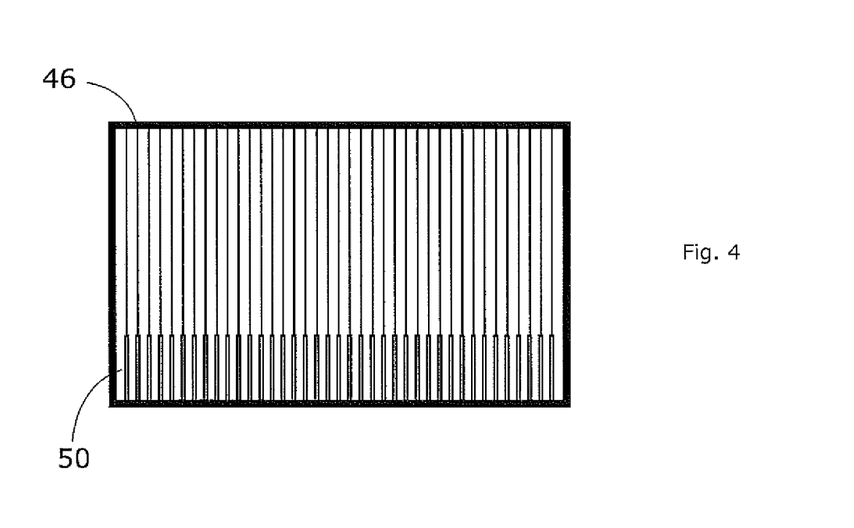
FIG. 4 is a cross-section view of the multi-leaf collimator shown in FIG. 3, along the line II.

Although not illustrated in FIG. 4, the leaves 48 may be thicker in parts further from the source of radiation 30 than parts nearer the source of radiation. That is, as the radiation beam diverges into the fan shape according to the present invention, so the leaves also increase in width so that the radiation beam is effectively blocked along the full length of the leaf 48.

The leaves 48 move only in the longitudinal direction. This makes the leaves short as they only have to traverse the small dimension of the collimator 32. As they are only moving a small distance the tip of each leaf can have a large radius and thereby minimise the radiation penumbra. Also, moving in this direction facilitates target tracking as targets generally move due to breathing and this is in a predominantly longitudinal direction.

Figure 5:
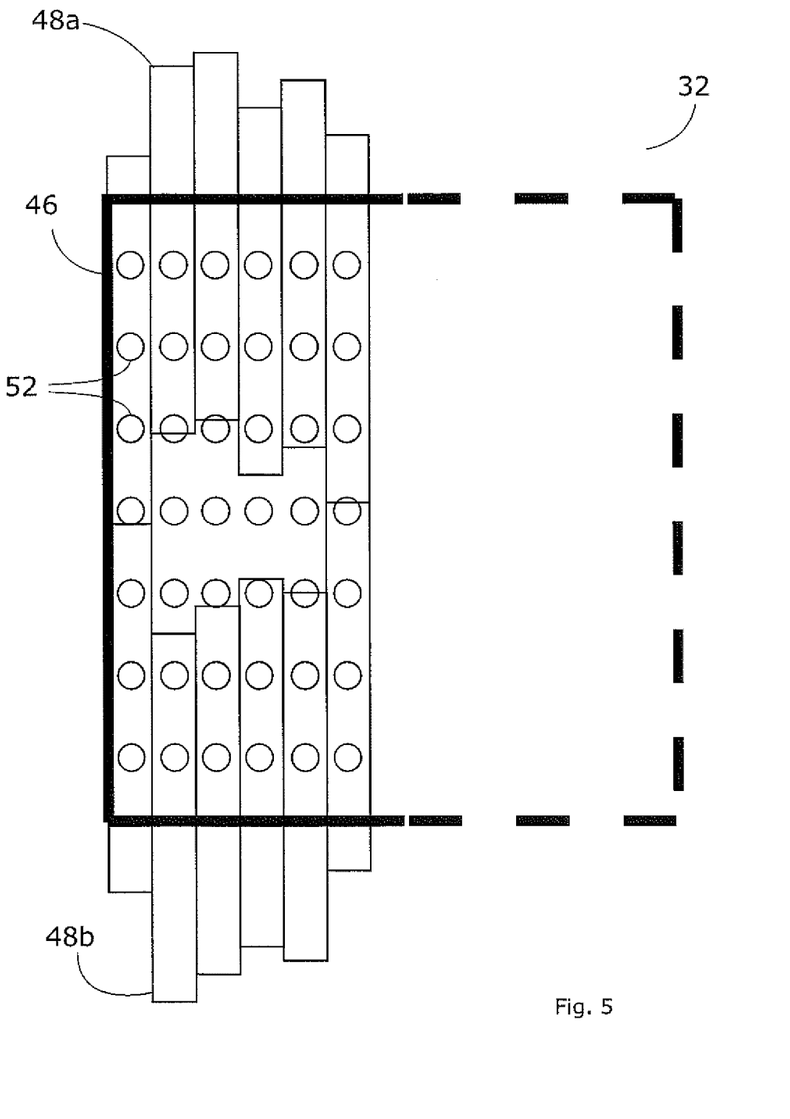
FIG. 5 shows a view of a multi-leaf collimator in which detector elements according to the embodiments of the present invention have been superimposed.

FIG. 5 shows a view of the multi-leaf collimator 32 on which detector elements 52 of the radiation detector 36 have been superimposed. Not all of the leaves 48 or detector elements 52 are shown for clarity. It can be seen that the detector elements 52 are arranged into columns which are aligned with the leaves 48 of the multi-leaf collimator. Specifically, a single column of detector elements 52 is aligned with a respective single leaf or single leaf pair 48. This allows detector 36 to perform quality assurance on the position of the leaves 48, but is generally insufficient for use as an imager of the region that is being targeted for therapy.

Figure 6:
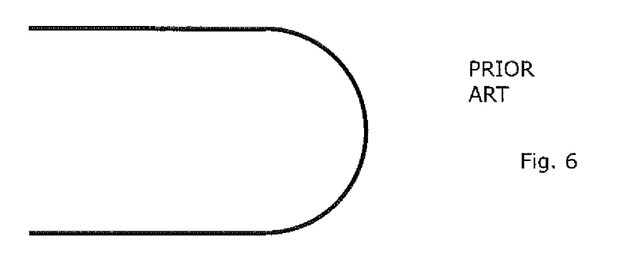
FIG. 6 shows the tip of a conventional leaf used in a multi-leaf collimator.
Figure 7:
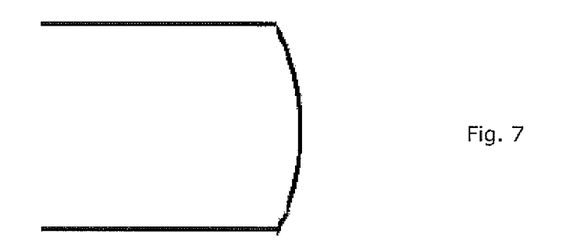
FIG. 7 shows the tip of a leaf according to an embodiment of the present invention.

FIG. 6 shows the tip of a conventional leaf. It can be seen that the tip is relatively rounded. FIG. 7 shows the tip of a leaf according to embodiments of the present invention. The tip has a much larger radius (i.e. is flatter with sharper edges) due to the short range of travel of the leaves across the aperture. The latter tip creates a sharper definition between areas in which radiation is allowed to pass through the MLC 32, and areas where the radiation is blocked. This increases the accuracy with which radiation can be applied to the patient.

The present invention therefore provides a system which incorporates both a radiotherapy apparatus and an MRI apparatus. A multi-leaf collimator is used to collimate and control the radiation beam before it impacts the patient. A radiation detector mounted opposite the source of radiation detects the radiation after it has passed through the patient, and may thus be used in quality assurance and in-vivo dosimetry. The detector has a resolution that is substantially equal to a width of the leaves in the multi-leaf collimator when projected onto the isocentric plane, as a high resolution is not required owing to the MRI apparatus.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A radiotherapy system comprising:
   a patient support, moveable along a translation axis;
   an imaging apparatus, comprising a first magnetic coil and a second magnetic coil, the first and second magnetic coils having a common central axis parallel to the translation axis, and being displaced from one another along the central axis to form a gap therebetween, the imaging apparatus being configured to obtain an image of a patient on the patient support;
   a source of radiation mounted on a chassis, the chassis being rotatable about the central axis and the source being adapted to emit a beam of radiation through the gap along a beam axis that intersects with the central axis;
   a multi-leaf collimator comprising a plurality of movable elongate leaves; and
   a radiation detector mounted to the chassis opposite the source, the radiation detector having a plurality of detector elements arranged in columns, each of the columns being superimposed with a respective elongate leaf of the elongate leaves when the plurality of detector elements and the plurality of elongate leaves are projected onto an isocentric plane and wherein the pitch between columns is equal to a width of the elongate leaves when projected onto the isocentric plane.

2. The radiotherapy system as claimed in claim 1, wherein the columns of detector elements are spaced between about 2 mm and about 10 mm apart when projected onto an isocentric plane.

3. The radiotherapy system as claimed in claim 1, wherein the radiation detector is mounted outside the first and second magnetic coils.

4. The radiotherapy system as claimed in claim 1, wherein the multi-leaf collimator further comprises a plurality of supports across the beam, for supporting the elongate leaves at least in their respective extended and intermediate positions.

5. The radiotherapy system as claimed in claim 1, wherein the multi-leaf collimator further comprises a respective plurality of pneumatic or hydraulic actuators, for moving the plurality of elongate leaves.

6. The radiotherapy system as claimed in claim 1, wherein the elongate leaves of the multi-leaf collimator are further moveable to a plurality of intermediate positions between their withdrawn and extended positions.

7. The radiotherapy system as claimed in claim 1, wherein the multi-leaf collimator is fixed in its rotation with respect to the source of radiation.

8. The radiotherapy system as claimed in claim 1, further comprising a control means for the source adapted to control the source so as to deliver a therapeutic radiation dose to a patient on the patient support, the control means being adapted to receive magnetic resonance images from the imaging apparatus during delivery of the dose.

9. The radiotherapy system as claimed in claim 1, in which the chassis is continuously rotatable about the central axis.

* * * * *